(12) United States Patent
Finley

(10) Patent No.: US 7,691,476 B2
(45) Date of Patent: Apr. 6, 2010

(54) HYDROPHILIC POLYMERIC COATINGS FOR MEDICAL ARTICLES

(75) Inventor: Michael J. Finley, Saint Louis Park, MN (US)

(73) Assignee: SurModics, Inc., Eden Prairie, MN (US)

( * ) Notice: Subject to any disclaimer, the term of this patent is extended or adjusted under 35 U.S.C. 154(b) by 849 days.

(21) Appl. No.: 11/445,806

(22) Filed: Jun. 2, 2006

(65) Prior Publication Data

US 2006/0276894 A1 Dec. 7, 2006

Related U.S. Application Data

(60) Provisional application No. 60/687,600, filed on Jun. 2, 2005.

(51) Int. Cl.
*B32B 9/04* (2006.01)

(52) U.S. Cl. .................................. 428/411.1; 428/423.1

(58) Field of Classification Search ............... 428/411.1, 428/423.1
See application file for complete search history.

(56) References Cited

U.S. PATENT DOCUMENTS

| 4,729,914 A | 3/1988 | Kliment et al. |
|---|---|---|
| 4,980,231 A | 12/1990 | Baker et al. |
| 5,290,585 A | 3/1994 | Elton |
| 5,414,075 A | 5/1995 | Swan et al. |
| 5,637,460 A | 6/1997 | Swan et al. |
| 5,645,931 A | 7/1997 | Fan et al. |
| 5,668,193 A | 9/1997 | Gouda et al. |
| 5,670,558 A | 9/1997 | Onishi et al. |
| 5,714,360 A | 2/1998 | Swan et al. |
| 5,731,087 A | 3/1998 | Fan et al. |
| 5,997,517 A | 12/1999 | Whitbourne |
| 6,087,415 A | 7/2000 | Vanderlaan et al. |
| 6,221,425 B1 | 4/2001 | Michal et al. |
| 6,238,799 B1 | 5/2001 | Opolski |
| 6,278,018 B1 | 8/2001 | Swan |
| 6,287,285 B1 | 9/2001 | Michal et al. |
| 6,306,176 B1 | 10/2001 | Whitbourne |
| 6,468,649 B1 | 10/2002 | Zhong |
| 6,534,559 B1 | 3/2003 | Vanderlaan et al. |
| 6,656,517 B2 | 12/2003 | Michal et al. |
| 6,706,025 B2 | 3/2004 | Engelson et al. |
| 6,709,706 B2 | 3/2004 | Zhong et al. |
| 6,866,936 B2 | 3/2005 | Opolski |
| 2003/0215649 A1 | 11/2003 | Jelle |

OTHER PUBLICATIONS

International Search Report for PCT/US2006/021296, Mar. 4, 2007, 5 pgs.

*Primary Examiner*—Thao T. Tran
(74) *Attorney, Agent, or Firm*—Kagan Binder, PLLC

(57) ABSTRACT

The invention provides a durable, lubricious coating for a medical article that can be prepared from a first polymer that is synthetic, soluble in a polar liquid, and having first reactive groups, and a second polymer that is synthetic, hydrophilic, and that includes second reactive groups. The first reactive groups and a portion of the second reactive groups react to bond the first polymer to the second polymer. A portion of the second reactive groups remains unbonded which, upon neutralization, provide lubricious properties to the coating. In some aspects the coating is formed using a crosslinking agent having latent reactive groups. The coatings provide particularly long dry out times and are very useful for catheterization processes. In addition, the coatings can be subject to sterilization with ethylene oxide and retain very good durable and lubricious properties.

18 Claims, No Drawings

HYDROPHILIC POLYMERIC COATINGS FOR MEDICAL ARTICLES

CROSS-REFERENCE TO RELATED APPLICATION

The present non-provisional Application claims the benefit of commonly owned provisional U.S. Patent Application having Ser. No. 60/687,600, filed on Jun. 2, 2005, and entitled HYDROPHILIC COATINGS INCLUDING POLYMERS HAVING REACTIVE GROUPS

FIELD OF THE INVENTION

The invention relates to hydrophilic polymeric coatings for surfaces of medical articles.

BACKGROUND OF THE INVENTION

Surface coatings can provide medical articles, such as those that are implanted or temporarily inserted into the body, with a variety of distinct benefits. These benefits include lubricity and wettability, passivity against protein absorption, antimicrobial properties, drug delivery, biocompatibility, and hemocompatibility. The demand for medical articles having these types of coatings is rapidly increasing because they generally improve the function of the device upon implantation or insertion in the body.

Coatings that have lubricious and wettable properties typically include hydrophilic materials. These hydrophilic materials reduce frictional forces when the device is introduced and moved within the body. Various catheter types are examples of medical articles that may be provided with hydrophilic coatings. Hydrophilic coatings are generally known in the art of implantable medical devices.

Providing hydrophilic coatings to medical devices can be particularly challenging from many standpoints. Many medical devices are twisted or contorted during use of the device in the body, which may result in cracking, or peeling of the coating. In addition, since hydrophilic coatings have the potential to swell to a certain extent in an aqueous environment, the components of the coating can potentially become dislodged and lost from the coating if not sufficiently stabilized. Given these factors, the coatings should adhere sufficiently to the device. Further, the dimensions and modulus of the device can be affected by coatings that are excessively thick. However, preparation of thin hydrophilic coatings can be difficult as a result of the properties of components that are used in the coating process.

Further, coatings are often prepared using organic solvents or low molecular weight monomeric compounds, which in some cases present toxicity concerns. While it is generally desirable to remove all solvent or unreacted low molecular weight monomeric materials, these components may remain in the coating in trace amounts. It is often necessary to properly handle these materials and remove them if they remain in the formed coating.

In addition to the general technical difficulties of producing a hydrophilic coatings that are compliant and durable, it can be difficult to keep a coated article sufficiently hydrated for a period of time prior to use. This period of time, generally commencing after removing the device from a wetting solution and before the device is inserted into a patient is referred to as "open time." During this period of time coatings can become dried out, resulting in discomfort to the patient upon insertion of the device. The drying may prompt rewetting of the coating, which, aside from adding to the insertion process, can increase the risk of infection.

In addition to those issues associated with device coating, in many cases it is desired to perform sterilization procedures on coated medical devices. Common sterilization procedures for medical devices include treating the device with ethylene oxide. However, coated polymeric materials can be sensitive to sterilization procedures, which may damage the coating by causing it to delaminate from the surface of the device or may alter the chemical properties of materials in the coating. For example, ethylene oxide sterilization can cause alkylation of the hydrophilic polymeric materials and greatly reduce the lubricity of the device.

SUMMARY OF THE INVENTION

The present invention is related to durable, lubricious coatings for medical articles and methods for the preparation thereof, particularly, medical articles that are inserted into a portion of the body. In one aspect, it has been discovered that medical articles provided with the coatings of the present invention can remain hydrated for a particularly long period of time following removal from a wetting solution. That is, the inventive coatings are relatively resistant to the effects of drying. The remarkably long dry out times are advantageous in many aspects, particularly in processes involving the insertion of the hydrated coated device in the body. For example, in instances where a patient is responsible for his or her own catheterization (self-catheterization; such as intermittent urinary self-catheterization) the coating of the present invention affords the patient with a prolonged insertion time, thereby providing increased safety and comfort.

In a fundamental form, the durable, lubricious coatings of the present invention are formed in a process involving a step of disposing a first polymer, which is synthetic, soluble in a polar liquid, and has a first reactive group; and a step of disposing a second polymer, which is synthetic, hydrophilic, and has a second reactive group. In the process, the first and second reactive groups react to form covalent bonds between the first and second polymers (a reacted pair). Analysis of the formed coating shows that the first reactive groups are at least substantially, or entirely, consumed in the coating process. Upon formation of the coating, a portion of the second reactive groups remains unreacted. The unreacted portion can be neutralized to provide a wettable coating. When wetted, the coating is durable, lubricious, and has exceptional water retention properties. The coating can be formed on all or a portion of the medical article.

In one aspect, the second reactive groups of the second polymer comprise pendent carboxylate groups. Upon contact with the first polymer, a portion of the carboxylate groups reacts with the first reactive groups, thereby bonding the second polymer to the first polymer. Upon wetting, the unbonded carboxylate groups provide the coating with the desirable lubricious properties. In preferred aspects, the second polymer that is used to form the second coated layer is a copolymer that includes (i) pendent reactive carboxylate groups, and (ii) pendent ester groups. Preferred ester groups have a short chain alkyl group such as $C_1$-$C_6$ alkyl, and more preferably $C_2$-$C_4$ alkyl. In other preferred aspects, the second polymer includes (i) pendent reactive carboxylate groups, and (ii) pendent ester groups having a mixture of $C_1$-$C_6$ alkyl groups. For example, a suitable copolymer of this type can be formed by reacting a maleic anhydride copolymer with an alcohol to yield a polymer derivative having carboxylate groups and ester groups (for example, ethyl or butyl half esters).

In some aspects the first reactive groups on the first polymer are carboxylate-reactive groups In some aspects, the carboxylate-reactive groups are selected from carbodiimide (—N=C=N—) or carbodiimide-containing groups. Preferably the first polymer is a poly(carbodiimide) having hydrophilic portions, which provide solubility in a polar liquid, such as water. The hydrophilic portions can be at the termini of the poly(carbodiimide) and can be cationic, anionic, or nonionic. Preferred water soluble poly(carbodiimides) include tetramethylxylylenecarbodiimide polymers having hydrophilic portions. The polymer of the first coated layer, such as those selected from poly(carbodiimides), also provides good compatibility in vivo. Preferably, the first polymer includes carbodiimide reactive groups and has a molecular weight of greater than about 1 kDa.

Since the compositions and methods of the present invention do not require the use of organic solvents or low molecular weight monomeric components, the invention also provides other advantages for improving both patient safety and preparer safety. The polymeric materials used herein are also suitable for contact with body tissues.

Another distinct benefit of the present invention is the ability to form a multi-layer coating in a very cost effective and efficient manner. The polymeric materials of the coating compositions are generally inexpensive and can be readily prepared or commercially obtained. These compositions can also be coated on the surface of medical articles with great ease, for example, by dip-coating, brush-coating, or sponge coating, and do not require the use of elaborate coating equipment or methods.

In other aspects of the invention, in addition to the first and second reactive groups, the coating can be formed using latent reactive groups, such as photoreactive groups. The latent reactive groups can provide additional bonding between the polymeric materials of the coating, and/or the surface of the device. Preferably, the latent reactive groups are provided on a cross-linking moiety. The bonding that is provided by the combination of the first and second reactive groups of the polymeric material and the latent reactive groups allow for the formation of durable, lubricious coatings with advantageous and improved properties.

Optionally, the latent reactive groups can be present on the first polymer, the second polymer, or combinations thereof. Although the bonding exists between the polymers of the first and second coated layers, additional bonding can be provided via activation of the latent reactive groups. This additional bonding provides a number of desirable advantages.

In one aspect of the invention where latent reactive groups are utilized, it is thought that their activation promotes not only the formation of a coating having an increased density of polymeric material, but also a coating that still retains desirable hydrophilic and lubricious properties. In this regard the coating can be wetted very rapidly, but also sufficiently to provide a lubricious surface. A coating formed using latent reactive groups can also demonstrate controlled swelling in an aqueous solution. It is thought that the bonding arrangement of polymeric material within the coating suppresses the ability of the coating to swell to a great extent.

This bonding arrangement in the coating is advantageous as there is not a considerable increase in the dimensions (for example, external dimensions) of the coated article upon wetting. Therefore, the invention provides a coating that can be hydrated and swell but not to the extent it impairs a function of the device. This feature can be particularly useful in various cases, for example, wherein the device itself is small, or in cases wherein it is desired that the coating does not significantly change the dimensions of the coated device, for example in the case of an inner lumen coating.

Therefore in some aspects, the polymeric material of the first coated layer is bonded, preferably covalently, to the hydrophilic polymer of the second coated layer via the first and second reactive groups, and one or more of the polymeric materials in the coating are further bonded together via the latent reactive groups, such as photoreactive groups.

Depending on the coating process employed, the coating of the invention can include ionic or non-ionic cross-linking agents having latent reactive groups. If desired, the coating can also include combinations of non-ionic and ionic cross-linking agents.

In some aspects a non-ionic photoactivatable cross-linking agent can be used. In one embodiment, the non-ionic photoactivatable cross-linking agent has the formula $XR_1R_2R_3R_4$, where X is a chemical backbone, and $R_1$, $R_2$, $R_3$, and $R_4$ are radicals that include a latent photoreactive group.

In other aspects, an ionic cross-linking can be used. For example, the ionic cross-linking agent is a compound having latent photoreactive groups according to formula I:

$$X_1\text{—}Y\text{—}X_2$$

where Y is a radical containing at least one acidic group, basic group, or a salt of an acidic group or basic group, and wherein $X_1$ and $X_2$ are each independently a radical containing a latent photoreactive group.

In some embodiments of the invention, in the formed coating, at least a portion of the cross-linking agents present in the coating have latent reactive groups that have been activated and reacted with one or more components of the coating and/or the surface of the device.

A coating having these features can be formed by various processes. For example, a coating can be formed by steps that include (a) disposing a first coating composition that includes a polymer having a first reactive group (b) disposing a second coating composition that includes polymer having a second reactive group, wherein either the first or second coating composition, or both the first or second coating composition, include a cross-linking agent comprising two or more latent reactive groups, and (c) applying energy to activate the latent reactive groups of the cross-linking agent. In the process, the energy can be applied at any time during and/or following disposing the cross-linking agent to activate the latent reactive groups of the cross-linking agent and cause the cross-linking of the polymeric materials within the coating and/or crosslinking of the polymers to the material of the medical article In some embodiments the coating is formed in a process comprising (a) disposing a composition comprising (i) a first polymer that is soluble in a polar liquid and comprising a first reactive group and (ii) a cross-linking agent comprising photoreactive groups and (b) disposing a composition comprising a (i) second polymer that is hydrophilic and comprising second reactive groups and (ii) a cross-linking agent having photoreactive groups. In preferred aspects, the cross-linking agent of the second coated layer is a non-ionic crosslinking agent.

In other embodiments the coating is formed in a process comprising (a) disposing a composition comprising (i) a first polymer that is soluble in a polar liquid and comprising a first reactive group and (b) disposing a composition comprising a (i) second polymer that is hydrophilic and comprising second reactive groups and (ii) a cross-linking agent having photoreactive groups. In preferred aspects, the cross-linking agent of the second coated layer is a non-ionic crosslinking agent.

In some embodiments the coating is formed in a process comprising (a) disposing a composition comprising (i) a first polymer that is soluble in a polar liquid and comprising a first reactive group and (ii) a cross-linking agent comprising photoreactive groups and (b) disposing a composition comprising a (i) second polymer that is hydrophilic and comprising second reactive groups.

In some embodiments the coating is formed in a process comprising (a) disposing a composition comprising a first polymer that is soluble in a polar liquid and comprising a first reactive group, (b) disposing a cross-linking agent comprising photoreactive groups and (c) disposing a composition comprising a second polymer that is hydrophilic and comprising second reactive groups.

The coatings of the invention are also durable and compliant. In one way, the durability is shown by the coatings having excellent lubricity after having been placed under physical challenge. It is thought that these features are due, at least in part, to very good adhesion between the first polymer and the surface of the device. The coatings also show resistance to cracking and delamination when the coated device is manipulated.

A coating having these properties is particularly useful for implantable medical devices, such as catheters, that experience considerable frictional forces during use. In these cases, the coating of the present invention is less likely to be abraded when the coated device is manipulated after its insertion in the body. That is, the coating is unlikely to fragment and produce coating residue that could be lost in vivo upon movement of device. Therefore, this feature (residue minimization) in turn provides related advantages, such as increased patient safety, extended use of the device life, and improved function of the device.

In another aspect, the invention also provides coatings that are particularly suitable for sterilization procedures. An exemplary sterilization procedure for insertable medical articles involves use of ethylene oxide as the sterilization agent. Ethylene oxide sterilization is widely used in the healthcare industry for the sterilization of medical articles. However, ethylene oxide treatment can have a detrimental affect on the material properties of various articles, in particular, those that have polymeric coatings. Ethylene oxide acts as a powerful alkylating agent that can alter surface chemistries by the addition of alkyl groups to certain moieties that may be present on the surface of articles. For some lubricous coatings, treatment with an ethylene oxide can reduce the lubricity associated with the coating (ethylene oxide inactivation). However, relative to hydrophilic coatings of the prior art, the coatings of the present invention provide increased resistance to inactivation by ethylene oxide.

A preferred coating for sterilization comprises a second polymer having pendent second reactive groups and pendent ether groups. The coatings maintain desired durability and lubricity after sterilization.

Therefore, in other aspects, the invention provides a method for preparing a sterile medical article having a hydrophilic coating. The method includes the steps of preparing a hydrophilic coating comprising a first and second polymer that are covalently bonded together. The second polymer comprises pendent second reactive groups and ester groups. The second reactive groups are preferably carboxylate groups which can be neutralized prior to wetting of the coating. More preferably the second polymer comprises a mixture of pendent carboxylate and pendent ether groups comprising $C_1$-$C_6$ alkyl groups. The method also includes a sterilization step, such as ethylene oxide sterilization.

DETAILED DESCRIPTION

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

The present invention is directed to methods for preparing hydrophilic coatings on the surface of medical articles. Generally, the coatings can be formed in a method that includes disposing a first polymer that is synthetic and soluble in a polar liquid, such as water, and that has a first reactive group. The first polymer can be disposed on the surface of a medical article or a portion thereof, or optionally on the top of one or more coated layers previously formed on the medical article. In doing so, a first coated layer containing the first polymer is formed.

After the first polymer is disposed, a second polymer that is synthetic, hydrophilic, and that has a second reactive group is disposed on the first layer. A portion of the second reactive groups becomes covalently bonded to the first reactive groups forming a reacted pair, bonding the second polymer to the first polymer. The second reactive groups that are not covalently bonded can be neutralized to provide a wettable and highly lubricious coating.

The coating process can provide a coating with two or more coated layers, that is, a first coated layer including the first polymer, and a second coated layer including the second polymer. Other coated layers are optional but may be formed depending on, for example, the type of medical article coated and the intended function of the article.

The first reactive group on the polymer of the first coated layer and second reactive group on the polymer that is hydrophilic are reactive with each other and define a reactive pair. Since the first coated layer and the second coated layer can be in contact with one another, the first and second reactive groups can be reacted to establish bonding between the polymer of the first coated layer and hydrophilic polymer of the second coated layer.

The durable, lubricious coatings of the invention can be formed on a wide variety of materials that have been used to fabricate the medical article or device. In order to define the polymeric material that can be present in a coated medical article, the materials that form the structure of the article are referred to herein as "article materials" or "device materials" whereas the materials used to form the polymeric coatings are herein referred to as "coating materials." In many cases, the medical article is formed from one or more biomaterial(s) as the coated article is typically placed in contact with biological fluids or tissues following implantation in the body).

A coating composition that includes the first polymer having the first reactive group can be suitable for providing a base coat to articles and devices that have a biomaterial surface, such as those fabricated from plastic and/or metal materials suitable for use in the body. While the first coating composition can be appropriately applied on any sort of biomaterial to form a first coated layer, a preferred biomaterial surface is fabricated from plastic materials. Exemplary plastic materials include polyvinylchloride (PVC), polytetrafluoroethylene (PTFE), polyethersulfone (PES), polysulfone (PS), polypropylene polyethylene, (PE), polyurethane (PU), polyetherimide (PEI), polycarbonate (PC), and polyetheretherketone (PEEK).

Metals that can be used in medical articles include platinum, gold, or tungsten, as well as other metals such as rhenium, palladium, rhodium, ruthenium, titanium, nickel, and alloys of these metals, such as stainless steel, titanium/nickel, nitinol alloys, and platinum/iridium alloys. These metals, including other alloys or combinations, can serve as suitable substrates for disposing the first coating composition.

Although many devices or articles are constructed from substantially all metal materials, such as alloys, some may be constructed from both non-metal and metal materials, where at least a portion of the surface of the device is metal. The metal surface may be a thin surface layer. Such surfaces can be formed by any method including sputter coating metal onto all or portions of the surface of the device.

Other surfaces that can be coated using the methods of the present invention include those that include human tissue such as bone, cartilage, skin and teeth; or other organic materials such as wood, cellulose, compressed carbon, and rubber. Other contemplated biomaterials include ceramics including, but not limited to, silicon nitride, silicon carbide, zirconia, and alumina, as well as glass, silica, and sapphire. Combinations of ceramics and metals can also be coated.

Metal and non-metal materials can be used to fabricate a variety of implantable articles or devices. The medical article or device can be any that is introduced temporarily or permanently into a mammal for the prophylaxis or treatment of a medical condition. These articles or devices include any that are introduced subcutaneously, percutaneously or surgically to rest within an organ, tissue, or lumen of an organ. In some aspects the coated medical article is inserted into a portion or portions of the urogenital system, such as the urethra. In some aspects the coated medical article is inserted into a portion or portions of the cardiovascular system, such as an artery, vein, ventricle, or atria of the heart.

The methods and materials of the invention can be utilized to coat virtually any medical article for which it is desired to provide a hydrophilic and lubricious coating on a surface thereof. In particular, the coatings are particularly useful for medical articles that can be inserted into and moved within the body.

Exemplary medical articles include vascular implants and grafts, grafts, surgical devices; synthetic prostheses; vascular prosthesis including endoprosthesis, stent-graft, and endovascular-stent combinations; small diameter grafts, abdominal aortic aneurysm grafts; wound dressings and wound management device; hemostatic barriers; mesh and hernia plugs; patches, including uterine bleeding patches, atrial septic defect (ASD) patches, patent foramen ovale (PFO) patches, ventricular septal defect (VSD) patches, and other generic cardiac patches; ASD, PFO, and VSD closures; percutaneous closure devices, mitral valve repair devices; left atrial appendage filters; valve annuloplasty devices, catheters; central venous access catheters, vascular access catheters, abscess drainage catheters, drug infusion catheters, parenteral feeding catheters, intravenous catheters (e.g., treated with antithrombotic agents), stroke therapy catheters, blood pressure and stent graft catheters; anastomosis devices and anastomotic closures; aneurysm exclusion devices; biosensors including glucose sensors; cardiac sensors; birth control devices; breast implants; infection control devices; membranes; tissue scaffolds; tissue-related materials; shunts including cerebral spinal fluid (CSF) shunts, glaucoma drain shunts; dental devices and dental implants; ear devices such as ear drainage tubes, tympanostomy vent tubes; ophthalmic devices; cuffs and cuff portions of devices including drainage tube cuffs, implanted drug infusion tube cuffs, catheter cuff; sewing cuff; spinal and neurological devices; nerve regeneration conduits; neurological catheters; neuropatches; orthopedic devices such as orthopedic joint implants, bone repair/augmentation devices, cartilage repair devices; urological devices and urethral devices such as urological implants, bladder devices, renal devices and hemodialysis devices, colostomy bag attachment devices; biliary drainage products.

To exemplify the benefits that the coatings of the present invention provide to medical devices, hydrophilic coatings on the surfaces of urogenital devices are discussed.

One exemplary device that can be coated to provide one or more hydrophilic surfaces is a urinary catheter. Urinary catheters are commonly used for the treatment of neuropathic bladder. Some urinary catheters are often referred to as "Foley catheters." The tubing of the catheter is typically made of silicone, latex, or polyvinyl chloride (PVC). In use, the catheter tubing is delivered through the urethra allowing for urine to drain from the bladder from the end of the urinary catheter located within the bladder. The end of the catheter that is located in the bladder typically has an aperture to let urine enter the tubing and a device, such as an inflatable balloon, that allows the end of the catheter to be held in the bladder. The end urinary catheter that is located outside the patient typically includes two tubes. One allows the passage of urine, and another tube can be used to provide a liquid such as sterile water or saline to the balloon to inflate it once the end of the catheter it is correctly positioned in the bladder.

As exemplified by a Foley-type urinary catheter, a hydrophilic coating both on the internal and external portions of the catheter tubing can improve function of the device. A coating on the external wall of the catheter can facilitate movement of the catheter within the lumen of the urethra, reducing the frictional forces during the insertion process. A coating on the internal wall of the catheter can facilitate movement of tubing that is movable within the lumen. In many embodiments, the catheter having an inventive coating as described herein can be sterilized to reduce the incidence of urinary tract infection.

Another type of urinary catheter is an intermittent urinary catheter. These intermittent catheters are typically inserted into a patient and then removed after the bladder has been drained. After the catheter has been wetted to increase its lubricity, a patient will typically perform the insertion and withdrawal of the intermittent catheter.

A hydrophilic coating of the present invention on at least the external portion of the catheter tubing can improve its function, particularly since the coating stays hydrated following wetting for a considerable period of time in ambient conditions (at least about 5 minutes and typically for about 15-20 minutes). This can provide the patient with time sufficient to appropriately insert the catheter, which can be very useful to patients who are not able to perform the insertion efficiently. The inventive coatings on intermittent urinary catheters therefore provide an approach to minimizing improper insertion and potential discomfort associated with insertion of a catheter that has lost its lubricity.

The hydrophilic coatings of the invention also reduce the risk of infection, as the user is more likely to successfully insert the catheter with one attempt at insertion. The likelihood of multiple rewettings, which increases the risk of infection, is reduced using catheters having the inventive coatings described herein.

Given this, the present invention can also provide a method for inserting a catheter into a portion of the body. The method can include the steps of obtaining a catheter comprising a hydrophilic coating of the present invention; wetting the catheter; and inserting the catheter into a portion of the body. In the method, the catheter is capable of remaining wetted for at least 5 minutes after the step of wetting without performing a step of re-wetting the catheter.

The durable, lubricious coatings of the invention can also be formed on the surfaces of endoscopic sheaths. Endoscopic sheaths can be used in various medical procedures, including those involving the urogenital tract, the gastrointestinal tract, and the vasculature. For example an endoscope can be delivered through an endoscopic sheath. Hydrophilic coatings on the internal and external walls of the endoscopic sheath can facilitate movement of the sheath in the body and the device within the sheath.

In some aspects of the invention, as exemplified by coatings that are provided to urinary catheters, a hydrophilic coating is formed on the external wall of the catheter. In some aspects the hydrophilic coating is formed using a photoreactive crosslinking agent. The photoreactive crosslinking agent can provide the exterior wall with increased durability, making the coating more resistant to abrasion by frictional forces from the urethral walls.

In other aspects, a hydrophilic coating can be formed on the internal wall of the catheter. In these preparations, a photoreactive crosslinking agent is optional, but typically not included in the coating. The photoreactive crosslinking agent may be excluded from the coating, as it is difficult to deliver light to internal walls of the device. The first and second reactive groups of the polymeric materials of the coating nonetheless allow coupling of the hydrophilic polymer of the second coated layer to the polymer of the first coated layer. While coatings on the exterior wall of the device that include the photoreactive crosslinking agent can provide coatings with excellent durability (among other improved properties), coatings provided to the interior of the device, formed without photoreactive crosslinking agent can still provide beneficial properties, and allow for improved use of the device.

Therefore the invention also provides methods for forming a lubricious coating on an inner wall (inner diameter) of a device. The method includes the steps of (a) forming a first coated layer on an inner wall that includes a first polymer comprising a first reactive group and (b) forming second coated layer on the first layer that includes a hydrophilic polymer comprising a second reactive group, wherein the hydrophilic polymer becomes bonded to the polymer of the first coated layer via reaction of the first and second reactive groups. For example, a water soluble carbodiimide polymer having is disposed on an inner wall and dried to form a first coated layer, and then a hydrophilic polymer comprising carboxylate groups can be disposed on the first coated layer to form a second coated layer, wherein the carboxylate group is reactive with the carbodiimide group, bonding the hydrophilic polymer carbodiimide polymer.

The coatings of the invention can be particularly useful for those devices that will come in contact with aqueous systems, such as bodily fluids. For example, a second coated layer that includes a hydrophilic polymer can improve the lubricity of the surface and can facilitate movement of the device in the body. In some cases, the second coated layer can include a hydrophilic polymer that can provide biocompatibility to the device surface and can minimize adverse reactions that may impair function of the coated device in the body.

In the coating processes described herein, the first and second coating compositions can be prepared without using hazardous organic solvents, and then (sequentially) disposed on the surface of a device, and dried. One advantage of the present coating compositions and processes is that, for example, a non-polar organic solvent is not required and therefore residual solvent and user contact with the solvent are not concerns.

Prior to disposing the first coating composition on the surface of the article, the article can be cleaned using any suitable technique.

While the coating of the present invention includes a first coated layer having a first polymer that is soluble in a polar solvent and that has a first reactive group, and a second coated layer that includes a polymer that provides a hydrophilic surface and has a second reactive group, the coating can also include other optional materials. For example, the coating can include other optional coated layers. As used herein, the term "layer" or "coated layer" will refer to a layer of one or more coated materials of sufficient dimensions (for example, thickness and area) for its intended use over the entire, or less than the entire, portion of an article surface. Therefore, a "coating" as described herein can include one or more "coated layers," each coated layer including one or more coating components. It is also understood that during the coating process, materials from one coated layer may migrate into adjacent coated layers, depending on the components of a particular coating composition, including the solvent or solution, and dissolved or suspended coating compounds. Therefore, to a certain extent, a coated layer may contain components from an adjacent coated layer.

One or more additional optional coated layers can be included in the coating on the article. Generally, if one or more additional optional coated layers are present in the coating, the additional layer(s) are located between the first coated layer and the surface of the device. Therefore, when referring to the step of disposing a first coating composition on a surface, the surface may be that of the device itself, or the surface of the device with one or more optional coated layers. For purposes of discussion these may be referred to as a third, forth, etc., coated layer.

An optional coated layer can facilitate formation of the first and second coated layers on the article. For example, the first polymer can be disposed on a medical device precoated with a non-polymeric silane compound. Exemplary, silane pre-coatings are described in U.S. Pat. No. 6,706,408.

These types of optional base coated layers can be particularly useful for providing a surface that can be reacted with a latent reactive group, such as a photoreactive group, pendent from a cross-linking agent that can be included in first coating composition.

According to the invention, a step in the coating process involves disposing a first polymer that is synthetic and having a first reactive group, wherein the first polymer is also soluble in a polar liquid. The polymer is "film forming" and has the properties of being able to be disposed on the surface of an article and form a coated layer. The first polymer can be a homopolymer or a copolymer having a first reactive group. The first reactive group of the polymer can react with the second reactive group (of the second polymer) that has an active hydrogen. In some aspects the first reactive groups can be selected from carboxylate-reactive, amine-reactive, and sulfhydryl-reactive groups. Preferred first reactive group are carboxylate-reactive and can be selected from carbodiimide (—N=C=N—) or carbodiimide-containing groups.

In preferred aspects the first reactive groups of the water-soluble polymer of the first coated layer are carbodiimide groups. A water-soluble poly(carbodiimide) refers to a polymer that includes carbodiimide groups (—N=C=N—) that can be dissolved in water. Such poly(carbodiimides) can be formed by the polymerization of monomers having isocyanate groups (O=C=N—), such as m-tetramethylxylylene diisocyanate, wherein the poly(carbodiimide) is further modified with a hydrophilic portion that provide the polymer with water soluble properties. The hydrophilic portion can be cationic and include, for example, a quaternary amine group, anionic and include, for example, a sulfonate group, or non-ionic and include, for example, polyether or polyester polymeric portions.

Suitable poly(carbodiimide) polymers for the first coated layer are available under the trade name Carbodilite™ commercially available from Nisshinbo Chemical and also described in U.S. Pat. No. 5,688,875.

In some aspects, the polymer of the first coated layer can include comonomers such as, vinyl monomers, and monomers that include aliphatic or non-polar groups.

A first coating composition can be prepared that includes the first polymer with a first reactive group, such as poly(carbodiimide), in an amount sufficient for the formation of a coated layer on the surface of the article. The coating composition including the first polymer preferably has a viscosity that is suitable for the type of coating process performed. In order to prepare a coating composition, the first polymer and any other optional component, can be dissolved or suspended in a suitable polar liquid. Exemplary polar liquids include alcohol or water. In preferred aspects, the viscosity of the coating composition is in the range of about 5 to 200 cP (at about 25° C.).

In preferred aspects the first polymer is dissolved or suspended at a concentration in the range of about 5% to about 20% (about 50-200 mg/mL), or more preferably about 5% to about 15% weight/volume (w/v). In some aspects, if more than one polymer is present in the first coating composition, the combined amount of polymeric materials can be in the ranges as described. In one exemplary preparation, the first coating composition includes poly(carbodiimide) at a concentration of about 10%.

In some aspects of the invention, a water soluble poly(carbodiimide) is included in the first coating composition. According to the invention, the water soluble poly(carbodiimide) is soluble in different polar liquids, including aqueous liquids, alcohol (such as isopropanol or ethanol), tetrahydrofuran (THF), toluene, and methyl ethyl ketone (MEK). One or more liquids can be chosen to provide a coating having a first coated layer with desired properties, such as a desired thickness. For example, a water soluble poly(carbodiimide) can be dissolved in an composition containing water or an alcohol to provide a thinner coating, or can be dissolved in THF, toluene, or MEK to provide a thicker coating. When the first coating composition is disposed on a substrate that includes a material such as PVC or latex, the THF, toluene, or MEK-based compositions can swell the substrate material. The swelling can cause the first polymer to become at least partially incorporated into the substrate material and can therefore improve the durability of the coating.

Preferred first coating compositions include a poly(carbodiimide) and an amount of alcohol, such as IPA, of about 30% or greater, and preferably in the range of about 30% to about 70%. Alcohol-based compositions are preferred as they are able to provide good wetting to substrates and also evaporate after the composition has been disposed on the surface.

The coating process can be carried out at a temperature suitable to provide a coating to the surface, or a portion of the surface, of the article or device. Preferably, the coating process is carried out at a temperature in the range of 10° C. to 50° C., and more preferably at a temperature in the range of 15° C. to 25° C. However, the actual coating temperature can be chosen based on aspects of the first coating composition, including the liquid used to dissolve or suspend the polymeric material, the polymeric material, and also the method used to dispose the first coating composition on the surface of the article or device.

The first coating composition can be applied to the surface of a device using any suitable technique. For example, the first coating composition can be dipped, sprayed, sponged, or brushed on a device to form a layer, and then dried. In some preferred embodiments, the first coating composition is applied by dip-coating. Optionally, the process can be repeated to provide a coating having multiple coated layers (multiple layers formed from the first coating composition). The suitability of the coating composition for use with a particular medical article, and in turn, the suitability of the application technique, can be evaluated by those skilled in the art, given the present description.

A preferred method for applying the coating composition is a straightforward method such as dip-coating. A typical dip-coating procedure involves immersing the article to be coated in the first coating composition, dwelling the object in the composition for a period of time (a standard time is generally less than about 30 seconds, and can even be less that 10 seconds in many cases), and then removing the article from the composition. After the article has been dip-coated in the coating solution, it is removed and dried. Drying can be carried out using any suitable method, including air-drying the dip coated article. Times up to 30 minutes can be sufficient to dry the coated article although shorter times may be also sufficient.

The processes described herein advantageously allow for the preparation of coatings having a desired thickness, but that are nonetheless durable and demonstrate excellent hydrophilic properties. In many aspects, the thickness can be tailored to fit the coating requirements of a user. This can be achieved by altering the coating parameters for the formation of the first coated layer that includes the water-soluble polymer with the first reactive group. For example, in some aspects the present inventive coating composition and methods allow for the formation of a relatively thin, but very durable coating.

In an exemplary preparation, the first coated layer has a thickness in the range of about 2 μm to about 3 μm (coating conditions can be altered or repeated to increase the thickness, such as up to about 10 μm) in a dried state. In addition to varying the liquid in the composition, the thickness of the coating can also be affected by changing the concentration of the polymer in solution. That is, increasing the concentration of the polymer can provide a thicker first coated layer, while decreasing the concentration of the polymer can provide a thinner first coated layer. The first coated layer is also compliant and conformal, meaning that it shapes well to the article to which is has been coated and that it can form to the changes in the shape of the device without introducing any substantial physical deformities.

In some aspects of the invention, a cross-linking agent is included in the first coating composition. In preferred aspects, the crosslinking agent includes two or more latent reactive groups. The latent reactive groups are activated when exposed to an appropriate activating source and can form bonds between the polymeric materials within the coating and/or the device surface. For example, when the crosslinking agent is included in the first coating composition, additional bonds can be formed between polymers in the first coated layer, between the polymer in the first coated layer and the surface of the device, or between first and second polymers in the coating (following the application of the second polymer).

Use of a crosslinking agent including latent reactive groups can improve the coating in various ways. For example, the crosslinking agent can improve the durability of the coating by creating additional bonding between the polymeric coating components and/or the polymeric coating components and the surface of the coated article. Activation of the latent reactive groups of the crosslinking is also thought to drive reaction between the first and second reactive groups, thereby further improving bonding between the first and second polymers and improving durability. In addition, use of a crosslinker with latent reactive groups is thought to promote the formation of a coating having an increased density of polymeric material. Swelling of the coating upon wetting can be controlled.

The use of a crosslinking agent with latent photoreactive groups can represent an improvement over conventional crosslinking agents which may be reactive with specific chemical groups, and which may not react with article materials.

If included in the first coating composition, the cross-linking agent can be included at a concentration that can improve the properties of the coating. For example, the cross-linking agent can be added in an amount to improve the durability, wetting properties, or resistance to reduction in the wettability as caused by sterilization processes. Exemplary amounts of the cross-linking compound present in the coating composition range from about 0.1% to about 3%, or about 0.5% to about 2.5% weight/volume (w/v). An exemplary amount of cross-linking agent added to the present coating composition is about 1% weight/volume (w/v).

Latent reactive groups, broadly defined, are groups that respond to specific applied external stimuli to undergo active specie generation with resultant covalent bonding to a target. Latent reactive groups are those groups of atoms in a molecule that retain their covalent bonds unchanged under conditions of storage but which, upon activation, form covalent bonds with other molecules. The latent reactive groups generate active species such as free radicals, nitrenes, carbenes, and excited states of ketones upon absorption of external electromagnetic or kinetic (thermal) energy. Latent reactive groups may be chosen to be responsive to various portions of the electromagnetic spectrum, and latent reactive groups that are responsive to ultraviolet, visible or infrared portions of the spectrum are preferred. Latent reactive groups, including those that are described herein, are well known in the art. The present invention contemplates the use of any suitable latent reactive group for formation of the inventive coatings as described herein.

Latent reactive groups include photoreactive groups that respond to specific applied external stimuli to undergo active specie generation with resultant covalent bonding to an adjacent chemical structure, for example, as provided by the same or a different molecule. Latent reactive groups, including photoreactive groups, are those groups of atoms in a molecule that retain their covalent bonds unchanged under conditions of storage but that, upon activation by an external energy source, can form covalent bonds with other molecules. See, for example, U.S. Pat. No. 5,002,582 (Guire et al., "Preparation of Polymeric Surfaces Via Covalently Attaching Polymers").

Photoreactive groups can generate active species such as free radicals and particularly nitrenes, carbenes, and excited states of ketones, upon absorption of electromagnetic energy. Photoreactive groups can be chosen to be responsive to various portions of the electromagnetic spectrum, and that are responsive to the ultraviolet and visible portions of the spectrum are preferred.

Photoreactive aryl ketones are preferred, such as acetophenone, benzophenone, anthraquinone, anthrone, quinone, and anthrone-like heterocycles (for example, heterocyclic analogs of anthrone such as those having nitrogen, oxygen, or sulfur in the 10-position), or their substituted (for example, ring substituted) derivatives. Examples of preferred aryl ketones include heterocyclic derivatives of anthrone, including acridone, xanthone, and thioxanthone, and their ring substituted derivatives. Some preferred photoreactive groups are thioxanthone, and its derivatives, having excitation energies greater than about 360 nm.

The functional groups of such ketones are preferred since they are readily capable of undergoing the activation/inactivation/reactivation cycle described herein. Benzophenone is a particularly preferred latent reactive moiety, since it is capable of photochemical excitation with the initial formation of an excited singlet state that undergoes intersystem crossing to the triplet state. The excited triplet state can insert into carbon-hydrogen bonds by abstraction of a hydrogen atom (from a support surface, for example), thus creating a radical pair. Subsequent collapse of the radical pair leads to formation of a new carbon-carbon bond. If a reactive bond (for example, carbon-hydrogen) is not available for bonding, the ultraviolet light-induced excitation of the benzophenone group is reversible and the molecule returns to ground state energy level upon removal of the energy source. Photoactivatable aryl ketones such as benzophenone and acetophenone are of particular importance inasmuch as these groups are subject to multiple reactivation in water and hence provide increased coating efficiency.

The azides constitute another class of photoreactive groups and include arylazides ($C_6R_5N_3$) such as phenyl azide and 4-fluoro-3-nitrophenyl azide; acyl azides (—CO—$N_3$) such as benzoyl azide and p-methylbenzoyl azide; azido formates (—O—CO—$N_3$) such as ethyl azidoformate and phenyl azidoformate; sulfonyl azides (—$SO_2$—$N_3$) such as benezensulfonyl azide; and phosphoryl azides [$(RO)_2PON_3$] such as diphenyl phosphoryl azide and diethyl phosphoryl azide.

Diazo compounds constitute another class of photoreactive groups and include diazoalkanes (—$CHN_2$) such as diazomethane and diphenyldiazomethane; diazoketones (—CO—$CHN_2$) such as diazoacetophenone and 1-trifluoromethyl-1-diazo-2-pentanone; diazoacetates (—O—CO—$CHN_2$) such as t-butyl diazoacetate and phenyl diazoacetate; and beta-keto-alpha-diazoacetatoacetates (—CO—$CN_2$CO—O—) such as t-butyl alpha diazoacetoacetate.

Other photoreactive groups include the diazirines (—$CHN_2$) such as 3-trifluoromethyl-3-phenyldiazirine; and ketenes (CH=C=O) such as ketene and diphenylketene.

Peroxy compounds are contemplated as another class of latent reactive groups and include dialkyl peroxides such as di-t-butyl peroxide and dicyclohexyl peroxide and diacyl peroxides such as dibenzoyl peroxide and diacetyl peroxide and peroxyesters such as ethyl peroxybenzoate.

If photoreactive groups are present on the cross-linking agent, preferably they are adapted to undergo reversible photolytic homolysis, thereby permitting photoreactive groups that are not consumed in attachment to a polymeric material to revert to an inactive, or "latent" state. These photoreactive groups can be subsequently activated, in order to attach to any compound in the coating, or the article material, with an abstractable hydrogen for covalent bond formation. Thus, excitation of the photo reactive group is reversible and the group can return to a ground state energy level upon removal of the energy source. In some embodiments, preferred cross-linking agents are those groups that can be subject to multiple activations and hence provide increased coating efficiency.

In situations in which all photoreactive groups and spacers are chemically, or at least functionally, the same, the distinction between first and second photoreactive groups can actually be accomplished at the time of the first activation step; that is, those groups that are activated and attach to the surface will be considered "first" photoreactive groups, and those that remain unreacted (whether or not they have been activated) will be considered "second" photoreactive groups.

The photoactivatable cross-linking agent can be ionic, and can have good solubility in an aqueous composition, such as the first and/or second coating composition. Thus, in some embodiments, at least one ionic photoactivatable cross-linking agent is used to form the coating. In some cases, an ionic photoactivatable cross-linking agent can crosslink the polymers within the second coating layer which can also improve the durability of the coating.

Any suitable ionic photoactivatable cross-linking agent can be used. In some embodiments, the ionic photoactivatable cross-linking agent is a compound of formula I:

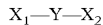

where Y is a radical containing at least one acidic group, basic group, or a salt of an acidic group or basic group. $X_1$ and $X_2$ are each independently a radical containing a latent photoreactive group.

The photoreactive groups can be the same as those described herein. Spacers can also be part of $X_1$ or $X_2$ along with the latent photoreactive group. In some embodiments, the latent photoreactive group includes an aryl ketone or a quinone.

The radical Y in formula I provides the desired water solubility for the ionic photoactivatable cross-linking agent. The water solubility (at room temperature and optimal pH) is at least about 0.05 mg/ml. In some embodiments, the solubility is about 0.1 to about 10 mg/ml or about 1 to about 5 mg/ml.

In some embodiments of formula I, Y is a radical containing at least one acidic group or salt thereof. Such a photoactivatable cross-linking agent can be anionic depending upon the pH of the coating composition. Suitable acidic groups include, for example, sulfonic acids, carboxylic acids, phosphonic acids, and the like. Suitable salts of such groups include, for example, sulfonate, carboxylate, and phosphate salts. In some embodiments, the ionic cross-linking agent includes a sulfonic acid or sulfonate group. Suitable counter ions include alkali, alkaline earths metals, ammonium, protonated amines, and the like.

For example, a compound of formula I can have a radical Y that contains a sulfonic acid or sulfonate group; $X_1$ and $X_2$ can contain photoreactive groups such as aryl ketones. Such compounds include 4,5-bis(4-benzoylphenylmethyleneoxy)benzene-1,3-disulfonic acid or salt; 2,5-bis(4-benzoylphenylmethyleneoxy)benzene-1,4-disulfonic acid or salt; 2,5-bis(4-benzoylmethyleneoxy)benzene-1-sulfonic acid or salt; N,N-bis[2-(4-benzoylbenzyloxy)ethyl]-2-aminoethanesulfonic acid or salt, and the like. See U.S. Pat. No. 6,278,018. The counter ion of the salt can be, for example, ammonium or an alkali metal such as sodium, potassium, or lithium.

In other embodiments of formula I, Y can be a radical that contains a basic group or a salt thereof. Such Y radicals can include, for example, an ammonium, a phosphonium, or a sulfonium group. The group can be neutral or positively charged, depending upon the pH of the coating composition. In some embodiments, the radical Y includes an ammonium group. Suitable counter ions include, for example, carboxylates, halides, sulfate, and phosphate. For example, compounds of formula I can have a Y radical that contains an ammonium group; $X_1$ and $k_2$ can contain photoreactive groups that include aryl ketones. Such photoactivatable cross-linking agents include ethylenebis(4-benzoylbenzyldimethylammonium) salt; hexamethylenebis (4-benzoylbenzyldimethylammonium) salt; 1,4-bis(4-benzoylbenzyl)-1,4-dimethylpiperazinediium) salt, bis(4-benzoylbenzyl) hexamethylenetetraminediium salt, bis[2-(4-benzoylbenzyldimethylammonio)ethyl]-4-benzoylbenzylmethylammonium salt; 4,4-bis(4-benzoylbenzyl)morpholinium salt; ethylenebis[(2-(4-benzoylbenzyldimethylammonio)ethyl)-4-benzoylbenzylmethylammonium] salt; and 1,1,4,4-tetrakis (4-benzoylbenzyl)piperzinediium salt. See U.S. Pat. No. 5,714,360. The counter ion is typically a carboxylate ion or a halide. On one embodiment, the halide is bromide.

In some aspects a non-ionic photoactivatable cross-linking agent can be used. In one embodiment, the non-ionic photoactivatable cross-linking agent has the formula $XR_1R_2R_3R_4$, where X is a chemical backbone, and $R_1$, $R_2$, $R_3$, and $R_4$ are radicals that include a latent photoreactive group. Exemplary non-ionic cross-linking agents are described, for example, in U.S. Pat. Nos. 5,414,075 and 5,637,460 (Swan et al., "Restrained Multifunctional Reagent for Surface Modification"). Chemically, the first and second photoreactive groups, and respective spacers, can be the same or different.

Some suitable cross-linking agents are those formed by a mixture of the chemical backbone molecule (such as pentaerythritol) and an excess of a derivative of the photoreactive group (such as 4-bromomethylbenzophenone). An exemplary product is tetrakis(4-benzoylbenzyl ether) of pentaerythritol (tetrakis(4-benzoylphenylmethoxymethyl)methane). See U.S. Pat. Nos. 5,414,075 and 5,637,460.

A single photoactivatable cross-linking agent or any combination of photoactivatable cross-linking agents can be used in forming the coating. In some embodiments, at least one nonionic cross-linking agent such as tetrakis(4-benzoylbenzyl ether) of pentaerythritol can be used with at least one ionic cross-linking agent. For example, at least one non-ionic photoactivatable cross-linking agent can be used with at least one cationic photoactivatable cross-linking agent such as an ethylenebis(4-benzoylbenzyldimethylammonium) salt or at least one anionic photoactivatable cross-linking agent such as 4,5-bis(4-benzoyl-phenylmethyleneoxy)benzene-1,3-disulfonic acid or salt. In another example, at least one nonionic cross-linking agent can be used with at least one cationic cross-linking agent and at least one anionic cross-linking agent. In yet another example, a least one cationic cross-linking agent can be used with at least one anionic cross-linking agent but without a non-ionic cross-linking agent.

The choice of a crosslinking agent may depend on the ingredients in the first or second coating composition. For example, a first coating composition that includes a poly (carbodiimide) in an aqueous liquid preferably includes an anionic crosslinking agent. However, a first coating composition that includes a poly(carbodiimide) in a liquid such as an alcohol or liquid such as THF, MEK, or toluene, preferably includes a nonionic crosslinking agent. Preferably, the second coating composition that includes the hydrophilic polymer is an alcohol-based composition that includes a non-ionic crosslinking agent.

If a cross-linking agent having latent reactive groups is included in the first coating composition, in some cases a step of irradiating may be performed to activate the latent reactive group. For example, the coating can be treated with UV irradiation following the step of disposing a first coating composition that includes a poly(carbodiimide) and a ionic photoactivatable cross-linking agent. The step of activating can be performed before and/or after the first coated layer dries. However, the step of activating may be performed at a later time during the coating process, such as after the second coating composition has been deposited on the substrate, or step of activating may be performed two or more times during the coating process.

Alternatively, the cross-linking agent having latent reactive groups can be deposited after the first coating composition has been deposited on the substrate. In these aspects, a high concentration of cross-linking agent can be made available at the interface of the first and second coated layers. Again, the step of activating may be performed after the cross-linking agent is disposed, and/or after the second coated layer is disposed.

Generally, the step of irradiating can be performed by subjecting the photoreactive groups to actinic radiation in an amount that promotes activation of the photoreactive group and bonding to a target moiety. In preferred aspects, the step of irradiating is performed after the second coating composition is disposed.

Actinic radiation can be provided by any suitable light source that promotes activation of the photoreactive groups. Preferred light sources (such as those available from Dymax Corp.) provide UV irradiation in the range of 190 nm to 360 nm. A suitable dose of radiation is in the range of from about 0.5 mW/cm$^2$ to about 2.0 mW/cm$^2$.

In some aspects, it may be desirable to use filters in connection with the step of activating the photoreactive groups. The use of filters can be beneficial from the standpoint that they can selectively minimize the amount of radiation of a particular wavelength or wavelengths that are provided to the coating during the activation process. This can be beneficial if one or more components of the coating are sensitive to radiation of a particular wavelength(s), and that may degrade or decompose upon exposure.

Typically, filters are identified by the wavelength of light that is permitted to pass through the filter. Two illustrative types of filters that can be used in connection with the invention are cut-off filters and band pass filters. Generally, cut-off filters are categorized by a cut-off transmittance, where the light transmittance is approximately 25% of the maximum transmittance. For band pass filters, a range of wavelength is identified for the filter, and the center wavelength is the midpoint of wavelength allowed through; at midpoint, the transmittance is approximately half of the maximum transmittance allowed through the filter. Thus, in one embodiment utilizing a band pass filter, for example, an Edmund 407 nm filter, the filter can be chosen that has a maximum UV transmittance at its center wavelength of 407 nm. In another embodiment, a band pass filter having a maximum transmittance at 500 nm is used.

After the first coated layer has been formed on a surface of an article, one or more steps can be performed to form the second coated layer that includes the second polymer which is synthetic, hydrophilic, and that has a second reactive group. The second polymer that is used to form the second coated layer can be a copolymer or a homopolymer.

As used herein, the term "hydrophilic" refers to a polymer that be wetted and retain water. A wetted coating provides the surface of the article with lubricity. As used herein, the term "lubricity" refers to a characterization of the frictional force associated with a coating. A coating with improved lubricity has a lower frictional force. Also, in many aspects, the coating has improved durability. As used herein, the term "durability" refers to the wear resistance of a polymer coating, or the ability of a coating to adhere to a device surface when subjected to forces typically encountered during use (for example, normal force, shear force, and the like). A more durable coating is less easily removed from a substrate by abrasion. Durability of a coating can be assessed by subjecting the device to conditions that simulate use conditions. Increased durability can be seen when the coated device is subject to mechanical or physical challenge, such as manipulation of the coated device by bending, twisting, or turning, and/or when the device is in contact with a portion of the body or a portion of another medical article.

The second coated layer can be formed by preparing a coating composition that includes a hydrophilic polymer having a pendent second reactive group that is reactive with the first reactive group of the polymer of the first coated layer. The second reactive group on the polymer of the second coated layer has an active hydrogen. In one preferred aspect the second reactive group is a pendent carboxylate group.

Other second reactive groups can include amine and sulfhydryl groups. A portion of the second reactive groups can be reacted with the first reactive group that is present on the polymer of the first coated layer.

In preferred embodiments, the hydrophilic polymer also includes pendent ester groups (—COOR$_1$). The pendent ester groups can have different alkyl chain lengths ($R_1$), wherein $R_1$ can be a short chain alkyl group such as a $C_1$-$C_4$ alkyl group.

In further preferred aspects, the hydrophilic polymer is a polymer that includes (i) carboxylate groups, and (ii) ester groups. Preferred ester groups have a short chain alkyl group such as $C_1$-$C_4$ alkyl group. These polymers can be prepared by the polymerization of a monomeric composition that includes maleic anhydride. These polymeric anhydrides can be reacted with an alcohol of the formula $R_1OH$ to provide a polymer having carboxylate and ester groups with a desired alkyl chain length ($R_1$). A polymer of this type therefore includes groups that are pendent from the polymer backbone that include oxygen atoms (carboxylate and ester groups) but that do not include oxygen atoms in the polymer backbone.

Preferred carboxylate and ester group-containing hydrophilic copolymers can also be obtained by copolymerizing a vinyl ether, such as methyl vinyl ether, with maleic anhydride, and then reacting with an alcohol to produce a copolymer having ether, ester, and carboxylate groups. One preferred and exemplary copolymer is a copolymer of methyl vinyl ether and maleic anhydride, wherein the copolymer is reacted with a $C_2$-$C_4$ alcohol. These copolymers can be commercially obtained under the trade name of Gantrez™ ES (for example Gantrez™ ES 225 or Gantrez™ ES 425) from International Specialty Products (Wayne, N.J.).

In the second coating composition, the hydrophilic polymer can be dissolved or suspended in a coating composition that includes a suitable solvent. In one mode of practice the second polymer is dissolved in an alcohol, such as isopropanol at a concentration that allows the formation of a second coated layer that has one or more desired properties, such as lubricity, durability, and/or other physical properties such as thickness. For example, the hydrophilic polymer can be prepared in a second coating composition at a concentration in the range of about 1% to about 20%, or about 5% to about 15% weight/volume (w/v). In some aspects, if more than one polymer is present in the first coating composition, the combined amount of polymeric materials can be in these ranges. An exemplary amount of first coating composition includes a methyl vinyl ether/maleic anhydride copolymer at a concentration of about 10%.

The concentration of the second polymer is sufficient to promote formation of a coating with a sufficient density of polymeric material, while at the same time having a viscosity that facilitates the coating process and allows formation of a coating with a desired thickness. For example, in some aspects, the first coating composition has a viscosity of less than about 200 cP. In preferred aspects the composition has a viscosity in the range of about 20 cP to about 60 cP. It has been found these relatively low viscosity compositions improve the coating process in many ways. For example, the coating process can be carried out rapidly. Aside from providing processing advantages, the low viscosity also minimizes any disruption of the first coated layer. In addition, the thickness and uniformity of the coating can be controlled with relative accuracy.

In an exemplary preparation, the second coated layer has a thickness in the range of about 3 μm to about 5 μm in a dried state. For coatings having the first and second layers, the overall coating thickness can be less than about 10 μm. In some preparations the coating has a thickness of about 5 μm. Upon wetting, a coating having the first and second coated layers can swell to a thickness in the range of about 100 μm to about 300 μm. However, use of a latent reactive group controls swelling of the coating so that the thickness of the coating is closer to 100 μm.

In some aspects, the formed coatings can have a lubricity of about 10 g or less. In some aspects the lubricity can be in the range of about 5 g to about 10 g.

In some embodiments a crosslinking agent having pendent latent reactive groups can be included in the second coating composition. Therefore, the second coated layer can be formed by disposing a second coating composition that includes the hydrophilic polymer and a cross-linking agent having a latent reactive group, and then treating the second coated composition to activate the latent reactive group of the cross-linking agent. Again, if a cross-linking agent is used in the composition it preferably includes photoreactive groups.

In some embodiments, the second coated layer is formed by a process that includes disposing a cross-linking agent that includes latent reactive groups, such as photoreactive groups, on the first coated layer prior to disposing the composition that includes the second polymer. For example, in some embodiments, a photoreactive cross-linking agent can be disposed on the first coated layer, followed by disposing the second coating composition, resulting in bond formation between the first and second reactive groups and also improving the bonding via the first and second reactive groups. Subsequently, the surface can be irradiated to activate the photoreactive group(s) of the cross-linking agent to further promote bond formation between and/or within the polymeric materials of the coating, for example between the polymer of the first coated layer and the second polymer.

The second coated layer can be formed in a manner that allows the second polymer to be coupled to materials of the first coated layer. Upon disposing the second coating composition, a portion of the second reactive groups react with the first reactive groups to form a covalent bond between the first and second polymers.

Other polymers can optionally be included in the second coating composition. Optional polymers can also be hydrophilic and synthetic, natural, or derivatives of a natural polymer.

Suitable optional synthetic hydrophilic polymers can be prepared from any suitable monomer including acrylic monomers or monomers bearing primary amines. Acrylic monomers include, for example, methacrylate, methyl methacrylate, hydroxyethyl methacrylate, hydroxyethyl acrylate, methacrylic acid, acrylic acid, glycerol acrylate, glycerol methacrylate, acrylamide, methacrylamide, and derivatives and/or mixtures of any of these. Examples of polymers that can be formed from these monomers include poly(acrylic acid), and poly(HEMA). Examples of hydrophilic copolymers include, for example, methyl vinyl ether/maleic anhydride copolymers, vinyl pyrrolidone/acrylic acid copolymers, and vinyl pyrrolidone/aminopropylmethacrylamide copolymers, and mixtures of any of these.

The inventive coatings can also include a colorant. A colorant can be provided along portions of the article surface to allow the progress of insertion of the article device into a patient to be monitored. The colorant(s) can provide a visual cue to the end user to indicate where the coating composition is located along the coated article (in other words, what portions of the device surface are in fact provided with a coating composition). The presence of a coating on a device surface is often determined by tactile means, meaning that the user can feel the portions of the device that are provided with a lubricious coating. A coating with a colorant can allow the user to visually determine the coated portions of the device, as compared to the more tactile methods. Being able to visually determine the coated portions of the device can improve also improve safety by reducing the handling of the device, which minimizes contamination by microorganisms. Further, when different coating compositions are provided on a device surface, distinct colorant can be provided for each coating composition, thereby providing a visual cue as to the identity and location of the different coating compositions.

The colorant can be present in any portion of the coating. For example, the colorant can be included in the composition including the first polymer, the composition including the second polymer, or both. In one aspect the colorant is included in the second composition. Optionally, the colorant can be included in a composition that is used to form a coated layer that is independent of either the first or second polymer.

Example of colorants that can be used in the preparation of coatings of the present invention include, but are not limited to, FD&C and D&C lakes, titanium dioxide, magnesium carbonate, talc, pyrogenic silica, iron oxides, channel black, insoluble dyes, natural colorants (such as riboflavin, carmine 40, curcumin, and annatto), dyes approved for ingestion by the U.S. Federal Drug Administration, or a combination of any of these. Colorants used in making coating dispersions for coating tablets, food, confectionery forms, agricultural seeds, and the like can be used in the coatings of the present invention.

The colorant can be present in one or more coated layers in an amount up to about 55% by weight of the non-liquid ingredients of the coating composition. In some exemplary modes of practice the colorant is used at about 1% wt/v in the coating composition. The composition that includes the colorant can also include a plasticizer. Exemplary plasticizers include propylene glycol, glycerol, and glycerin.

After the coating has been formed on the surface of a device (such as a catheter, for example) the coated device can optionally be sterilized prior to use. While any type of sterilization procedure can be employed, one preferred procedure involves treatment with ethylene oxide. The coated device can be obtained and subject to a sterilization process, such as ethylene oxide sterilization, or a user can perform the steps of forming a hydrophilic coating and then also perform sterilizing the coated device.

Sterilization with ethylene oxide offers the advantage of avoiding the higher temperatures or the moisture associated with steam sterilization. Another advantage of ethylene oxide is that its residues volatilize relatively quickly from the article sterilized. Since ethylene oxide is a highly flammable material it is generally used in a mixture with a flame retardant. Commonly used flame retardant compounds include chlorofluorocarbons (CFCs) such as dichlorodifluoro-methane (also known as CFC 12), and carbon dioxide. Other components that can be present in mixture with ethylene oxide include inert nitrogen gas, which may be used to increase the pressure in the sterilization chamber.

An exemplary ethylene oxide sterilization is carried out as follows. The coated device is place in a commercially available sterilization chamber. The chamber is then heated to a temperature within the range of from about 54° C. (130° F.) to about 60° C. (140° F.). A partial vacuum is created in the chamber with the addition of water vapor to provide a relative humidity in the range of about 30 to about 80 percent. The sterilant mixture is then converted to a vapor and introduced into the sterilization chamber at a pressure in the range of about 362.0 millimeter of mercury (0° C.; 7 psi) to about 1706.6 millimeter of mercury (0° C.; 33 psi). The sterilization time can vary and is dependent upon a number of factors including temperature, pressure, humidity level, the specific sterilant mixture employed, and the coated device. Following exposure the ethylene oxide is evacuated from the chamber, for example, by flushing with air, nitrogen, steam or carbon dioxide.

Second polymers having pendent ester groups have been found to be particularly useful for the preparation of lubricious and durable coatings that are also subject to ethylene oxide sterilization. Given this, a coating can be formed comprising a first coated layer comprising a first polymer having a first reactive group bonded to a second reactive group that is present on a second polymer, the second polymer being hydrophilic. The second polymer also includes pendent second reactive groups that are not bonded, and pendent ester groups. The coating can also include a cross-linking agent having latent reactive groups that have been activated to provided additional bonding between the polymeric materials of the coating. The coating can then be sterilized using ethylene oxide.

The invention will be further described with reference to the following non-limiting Examples.

Friction Testing—Vertical Pinch Test

After applying the inventive coating composition to the substrates, the coated substrates were evaluated for lubricity/durability by friction measurements using a Vertical Pinch Method, as described in International Application Number WO 03/055611 with the following modifications. The coated substrates samples were inserted into the end of a rod holder, which was placed between the two jaws of a pinch tester and immersed in a cylinder of water or saline. The jaws of the pinch tester were closed as the sample was pulled in a vertical direction and opened when the coated sample was returned to the original position. A 500 g force was applied as the coated substrates were pulled up through the pinched jaws. The pull force exerted on the substrate was then measured (grams). Pull force (g) is equal to the coefficient of friction (COF) multiplied by pinch force (g). The average frictional force was determined for 5 cycles while the coated substrates traveled 10 cm at a travel rate of 1 cm/sec

EXAMPLE 1

PVC urinary catheter tubing (Oy Fluorplast; Petalax, Finland) and Pebax rods (3 mm O.D.; Medsource, Inc., MN) was dip-coated for ten seconds into a solution of photoactivatable cross-linking agent #1, tetrakis(4-benzoylphenylmethoxymethyl)methane prepared as described in U.S. Pat. No. 5,414,075 Example 1, at a concentration of 1 mg/ml, and 100 mg/ml of polycarbodiimide (Dow Chemical UCARLNK™ XL 29SE) in THF. After fifteen minutes of air drying, the samples were dip-coated for ten seconds into a solution of 100 mg/mL of poly(methylvinylether-co-maleic anhydride butyl ester) (Gantrez™ ES 425; International Specialty Products (Wayne, N.J.) and 1 mg/ml of the cross-linking agent in a solution of 90% isopropanol/10% ethanol. After another air-drying, UV illumination was performed with a Dymax lamp (model no. PC-2, Dymax Corporation, Torrington, Conn.) having a Heraeus bulb (W. C. Heraeus GmbH, Hanau, Federal Republic of Germany). The coated substrates were suspended midway between the opposed Dymax lamps, approximately 40 cm apart. The illumination duration was for 3 minutes at an intensity of 1-2 mW/cm$^2$ in the wavelength range of 330-340 nm.

EXAMPLE 2

Polyvinyl chloride (PVC) urinary catheter tubing and Pebax rods as prepared in Example 1 were dipped in 20 mg/mL aqueous sodium bicarbonate and then packaged in Dual-Peel pouches and sent for ethylene oxide sterilization. Samples were tested using the Vertical Pinch Test method for friction force. A very slippery and durable coating was observed on the sample materials after hydration. They exhibited average vertical pinch friction forces of less than 30 grams. Uncoated control samples exhibit average vertical pinch friction forces of over 450 grams. All tested material stained very intensely with toludine blue. Hydrated samples were suspended in air at room temperature and 30% relative humidity. They remained slippery to a finger rub for over twenty minutes. Sample catheters and Pebax rods coated with a comparison coating of poly(vinylpyrrolidone) were not slippery to a finger rub within three minutes.

EXAMPLE 3

A cleaned Pellethane polyurethane chest access catheter was dipped for 30 seconds into 10% polycarbodiimide (Carbodilite™; Nisshinbo Industries, Inc, Japan) in 60% isopropanol. After 15-minute air dry, the rod was dipped for ten seconds into a solution of 100 mg/mL of poly(methylvinylether-co-maleic anhydride butyl ester) (Gantrez™ ES 425; International Specialty Products (Wayne, N.J.) and 0.5 mg/mL tetrakis(4-benzoylphenylmethoxymethyl)methane (photoactivatable cross-linking agent #1) in a solution of 90% isopropanol/10% ethanol, and then air-dried overnight at room temperature. The next day, the catheter was treated for three minutes with the UV lamps as previously described. After a soak in aqueous sodium bicarbonate and a water rinse, a one-minute wet finger rub showed that the rod displayed a very slippery and durable coating. The vertical pinch friction tester showed an average force of 5 to 10 grams. An uncoated control sample showed an average friction force of over 450 grams.

EXAMPLE 4

A clean Pebax rod was dipped for into a solution of 10% polycarbodiimide and air-dried for 15 minutes as described in Example 1. Next, the primed rod was dipped into a 50 mg/mL aqueous solution of poly(methylvinylether-co-maleic acid) (Gantrez™ S97 BF; International Specialty Products (Wayne, N.J.) and 0.5 mg/mL photoactivatable cross-linking agent #2, 4,5-bis(4-benzoylphenylmethyleneoxy)benzene-1,3-disulfonic acid, prepared as described in U.S. Pat. No. 6,278,018, Example 1, and air dried for two hours. The rod was treated for three minutes with UV lamps as previously described, soaked in a sodium bicarbonate solution and rinsed with water prior to testing for average friction force. The test showed a mean average friction force of between 10 and 20 grams. A one-minute wet finger rub showed that the coated rod was very slippery and durable. An uncoated Pebax rod shows a vertical pinch friction test result of over 450 grams.

EXAMPLE 5

Polypropylene flats that were coated generally using the process as described in Example 1 (without use of the crosslinking agent), and then were subject to FTIR microanalysis. Control samples included (a) the flats coated with the polycarbodiimide alone ((a-1)UCARLNK™XL 29SE; (a-2) Carbodilite™) and (b) the flats coated with the poly(methylvinylether-co-maleic anhydride butyl ester) alone (without the presence of the polycarbodiimide primary coat, the poly(methylvinylether-co-maleic anhydride butyl ester) washed off upon contact with a wetting solution). FTIR microanalysis was performed on each sample using an ATR objective with a depth penetration of approximately 0.5 μm. The carbodi-imine functional group (N=C=N) of the polycarbodiimide was analyzed, having a strong peak around 2130 $cm^{-1}$. The polypropylene substrate on which the coatings were formed did not produce any interfering peaks in the region of interest. The FTIR analysis indicated that the polycarbodiimide samples had a dramatic decrease in the N=C=N peak (~2115 $cm^{-1}$) once the poly(methylvinylether-co-maleic anhydride butyl ester) was formed on the polycarbodiimide primary coat. A peak shift for the N=C=N peak from 2130 $cm^{-1}$ to around 2115 $cm^{-1}$ was most likely due to the influence of the surrounding functional groups in the carbodiimide compound. When polycarbodiimide was added to the poly(methylvinylether-co-maleic anhydride butyl ester), the amount of residual N=C=N was quite low as indicated by the small peak around 2125 $cm^{-1}$.

Analysis of the formed coating shows that the carbodiimine functional groups are at least substantially, or entirely, consumed in the coating process. However, free carboxylate groups remain following application of the poly(methylvinylether-co-maleic anhydride butyl ester), since, following neutralization, the samples were able to be wetted and demonstrated lubricity.

I claim:

1. A medical article having a durable, lubricious coating comprising:
   a first coated layer comprising a first polymer that is synthetic and soluble in a polar liquid, and
   a second coated layer comprising a second polymer that is synthetic and hydrophilic, wherein the first polymer and second polymer are covalently bonded via a reacted pair comprising first and second reacted groups, wherein the second polymer comprises pendent second groups that are not bonded to the first polymer and which contribute to the lubricious property of the coating, and wherein the second polymer further comprises pendent ester groups.

2. The medical article of claim 1 where the second reacted groups comprises pendent reacted carboxylate groups.

3. The medical article of claim 1 where the ester groups of the second polymer comprise $C_1$-$C_6$ alkyl groups.

4. The medical article of claim 3 where the ester groups of the second polymer comprise $C_2$-$C_4$ alkyl groups.

5. The medical article of claim 4 where the second polymer comprises a maleic anhydride copolymer.

6. The medical article of claim 1 where the first polymer comprises a poly(carbodiimide) having hydrophilic segments.

7. The medical article of claim 6 where the first polymer comprises a tetramethyl-xylylenecarbodiimide polymer.

8. The medical article of claim 1 where the coating has a thickness of 10 μm or less in a dried state.

9. The medical article of claim 1 wherein the coating comprises a crosslinking compound comprising photoreactive groups.

10. The medical article of claim 9, wherein the crosslinking compound is an ionic crosslinking compound.

11. The medical article of claim 9, wherein the crosslinking compound is non-ionic.

12. The medical article of claim 1 wherein the medical article comprises a catheter.

13. The medical article of claim 1 wherein the medical article comprises a urinary catheter.

14. The medical article of claim 1, which is sterilized.

15. The medical article of claim 14, which has been sterilized with ethylene oxide.

16. The medical article of claim 1 comprising a substrate material, wherein the first polymer is at least partially incorporated into the substrate material.

17. The medical article of claim 16 wherein the substrate material comprises PVC or latex.

18. A sterilized medical article having a durable, lubricious coating comprising:
   a first coated layer comprising a first polymer that is synthetic and soluble in a polar liquid, and
   a second coated layer comprising a second polymer that is synthetic and hydrophilic, wherein the first polymer and second polymer are covalently bonded via a reacted pair comprising first and second reacted groups, wherein the second polymer comprises pendent second groups that are carboxylate groups which are not bonded to the first polymer and which contribute to the lubricious property of the coating, and wherein the second polymer further comprises pendent ester groups.

* * * * *